(12) United States Patent
Cavani et al.

(10) Patent No.: US 7,557,223 B2
(45) Date of Patent: Jul. 7, 2009

(54) TITANIUM-VANADIUM-TIN COMPRISING CATALYST AND PROCESS FOR THE PREPARATION OF PHTHALIC ANHYDRIDE

(75) Inventors: Fabrizio Cavani, Modena (IT); Carlo Fumagalli, Albano San Alessandro (IT); Roberto Leanza, Milan (IT); Gianluca Mazzoni, Torre Boldone (IT); Barbara Panzacchi, Bologna (IT)

(73) Assignee: Lonza Spa, Scanzorosciate (IT)

( * ) Notice: Subject to any disclaimer, the term of this patent is extended or adjusted under 35 U.S.C. 154(b) by 1115 days.

(21) Appl. No.: 10/517,816

(22) PCT Filed: Jun. 19, 2003

(86) PCT No.: PCT/EP03/06494

§ 371 (c)(1),
(2), (4) Date: Dec. 14, 2004

(87) PCT Pub. No.: WO04/000455

PCT Pub. Date: Dec. 31, 2003

(65) Prior Publication Data

US 2005/0240031 A1 Oct. 27, 2005

(30) Foreign Application Priority Data

Jun. 19, 2002 (IT) .......................... MI2002A1358

(51) Int. Cl.
*C07D 307/77* (2006.01)
(52) U.S. Cl. ..................................... 549/240
(58) Field of Classification Search ................. 549/240
See application file for complete search history.

(56) References Cited

U.S. PATENT DOCUMENTS

| 4,448,898 | A | 5/1984 | Sun |
| 4,469,878 | A | 9/1984 | Kaneyasu et al. |
| 4,879,387 | A | 11/1989 | Hara |
| 6,369,240 | B1 | 4/2002 | Hara et al. |

FOREIGN PATENT DOCUMENTS

| DE | 1943759 | 4/1971 |
| EP | 0286448 | 10/1988 |
| EP | 0985648 | 3/2000 |

OTHER PUBLICATIONS

Applicants' corresponding International Search Report.
Wainwright, M.S., et al., *Catal. Rev.-Sci. Eng*, 19 (1979)211.
Nikolov, V., et al., *Catal. Rev. Sci. Eng.*, 33 (1991)319.
Dias, Christina R., et al., *Catal. Rev. Sci. Eng.*, 39(1997)169.
Centi, G., G. Centi, Appl. Catal., A:general, 147 (1996)267.

*Primary Examiner*—Taofiq A. Solola
(74) *Attorney, Agent, or Firm*—Polsinelli Shughart PC; Lisa V. Mueller

(57) ABSTRACT

Catalytic compositions of oxides of titanium, vanadium and tin that are suitable for the production of phthalic anhydride by oxidizing o-xylene and/or naphthalene in the gas phase. The catalysts exhibit excellent activity and selectivity. The catalyst contains 2 to 15 percent by weight (calculated as $V_2O_5$) of vanadium, 1 to 15 percent weight (calculated as $SnO_2$) of tin and 70 to 97 percent by weight (calculated as $TiO_2$) of titanium. In a preferred embodiment the catalyst also contains up to 5 percent by weight (calculated as $M_2O$) of at least one alkali metal, preferably lithium, potassium or rubidium, and more preferably cesium. In an even more preferred embodiment, cesium is present in an amount of from 0.01 to 2 percent by weight (calculated as $Cs_2O$).

20 Claims, No Drawings

TITANIUM-VANADIUM-TIN COMPRISING CATALYST AND PROCESS FOR THE PREPARATION OF PHTHALIC ANHYDRIDE

This application is a 371 national stage application of International (PCT) Application No. PCT/EP03/006494, filed on Jun. 19, 2003, that has priority benefit of Italian Patent Application No. MI2002A001358, filed on Jun. 19, 2002.

The present invention relates to a catalyst for the selective oxidation of o-xylene, naphthalene, or a mixture of both to phthalic anhydride in the gas-phase, using a gas containing molecular oxygen, preferably air. The catalyst is characterised by a high activity and a high selectivity to phthalic anhydride. It further relates to a process for the preparation of said catalyst and a process for the production of phthalic anhydride employing said catalyst.

Phthalic anhydride is an important chemical intermediate used for the production of plasticizers, alkyd resins, unsaturated polyester resins and other commercial products.

The commercial production of phthalic anhydride is based on the gas phase oxidation of o-xylene, naphthalene, or a mixture of both. The oxidation is performed by feeding a mixture of the hydrocarbon(s) and an oxygen containing gas, usually air, over a fixed bed of catalyst in a tubular reactor tube at temperatures in the range of 300-400° C. Commercially the oxidation is carried out in multitubular fixed-bed reactors. The reaction is exothermic and the heat of reaction is removed by cooling media, usually molten salts, circulating in the shell around the reactor tubes. In spite of the cooling, the reactor is not isothermal and a temperature profile with a hot spot develops along the tube from inlet to outlet. These local hot spots are undesired because they may damage the catalyst and favour the formation of undesired side products, such as maleic anhydride, benzoic acid, carbon monoxide and carbon dioxide. In order to limit the formation of hot spots, catalyst beds with two or three different catalysts, with graduated activity, are often used. Their activity is lowest at the entrance of the reactants, where most of the heat is formed, and highest at the outlet of the catalyst bed (U.S. Pat. No. 6,362,345). The use of a highly active catalyst, especially in the lower part of the bed, i.e., near the entrance of the reactants, allows to carry out the reaction at lower temperature, with advantages for the yield of the reaction and the life of the catalyst. Therefore it has been very desirable to develop highly active catalyst compositions which at the same time have a high selectivity for phthalic anhydride.

The catalysts used today for the production of phthalic anhydride are usually supported catalysts wherein the catalytically active material is deposited, preferably as a coating, on an inert support in the form of granules or pellets, usually in the shape of spheres, cylinders or rings. The inert support in the granules or pellets of the catalyst may be, for example, corundum, steatite, alumina, silicon carbide or any other material having suitable chemical inertness and mechanical and thermal stability. The amount of active material deposited on the inert carrier is usually between 1 and 15 wt. %, based on the total weight of the catalyst.

The active material of the catalysts currently being used in the production of phthalic anhydride generally comprises titanium dioxide (titania), preferably having the crystalline structure of anatase, vanadium oxide, which is spread over the titanium dioxide and chemically interacts with it, and various additional components which are referred to as dopants. The dopants include elements like cesium, antimony, molybdenum, potassium, phosphorus and mixtures thereof. They are either:

(i) alkali metal or alkaline earth metal ions, the role of which is claimed to tune the surface acid-basic properties of the catalyst—alkali or alkaline earth metal ions are generally known to increase the selectivity and to decrease the activity of the catalysts (M. S. Wainwright, N. R. Foster, *Catal. Rev. Sci. Eng.*, 19 (1979) 211; V. Nikolov, D. Klissurski, A. Anastasov, *Catal. Rev. Sci. Eng.*, 33 (1991) 319; C. R. Dias, M. Farinha Portela, G. C. Bond, *Catal. Rev. Sci. Eng.*, 39 (1997) 169)—or (ii) transition or post-transition metal ions, the role of which is claimed to be the control of the redox properties of vanadium ions (M. S. Wainwright, N. R Foster, *Catal. Re. Sci. Enig.*, 19 (1979) 211; V. Nikolov, D. Klissurski, A. Anastasov, *Catal. Rev. Sci. Etig.*, 33 (1991) 319; C. R. Dias, M. Farinha Portela, G. C. Bond, *Catal. Rev. Sci. Eng.*, 39 (1997) 169); which are considered to be the main active sites in the reaction.

Another role of dopants can be the stabilization of the morphological features of titanium dioxide, such as crystallinity and surface area, or the formation of compounds with vanadium oxide having peculiar properties.

In the oxidation of o-xylene or naphthalene, besides phthalic anhydride several by products are formed, including carbon monoxide, carbon dioxide, o-tolualdehyde, o-toluic acid, phthalide, maleic anhydride and benzoic acid. In particular, these by-products are formed in hot spots which can develop in the reactor tubes as decribed above. These by-products are particularly undesired because they decrease the conversion and the yield of phthalic anhydride and some of them are difficult to remove. In commercial application, the conversion of o-xylene must be as high as possible and, consequently, the concentration of unconverted o-xylene at the reactor outlet must be as low as possible. Thus the optimal catalyst has to be as active as possible, so to achieve a very high o-xylene conversion, and also very selective in phthalic anhydride, leading to as low an amount as possible of by-products.

The activity of the catalysts can be increased in different ways:

1) Increasing the surface area of titania, so to achieve a higher dispersion of vanadium active sites (G. Centi, *Appl. Catal., A: general*, 147 (1996) 267, and references cited therein). The main drawback of this approach is that higher surface areas usually result in catalysts which are less resistant towards thermal shocks and local hot-spots, and more easily tend to exhibit recrystallization phenomena with segregation of vanadium oxide, responsible for a decrease of the surface area and progressive decrease of the activity of the catalyst.

2) Loading a higher amount of vanadium oxide while keeping the surface area of titania constant (G. Centi, *Appl. Catal., A: general*, 147 (1996) 267, and references cited therein). The disadvantage of this approach is that it is known that an optimal amount of vanadium exists for a given titanium dioxide surface area, which corresponds to the formation of the so-called "monolayer" of active species. Higher amounts of vanadium oxide are useless and deleterious, since bulk vanadium oxide may form which does not interact with the titanium dioxide and worsens the selectivity of the catalyst towards phthalic anhydride.

3) Using suitable dopants to improve the activity of the catalyst while maintaining good performance in terms of selectivity to phthalic anhydride (M. S. Wainwright, N. R. Foster, *Catal. Rev. Sci. Eilg.*, 19 (1979) 21 1; V. Nikolov, D. Klissurski, A. Anastasov, *Catal. Rev. Sci. Eng.*, 33 (1991) 319; C. R. Dias, M. Farinha Portela, G. C. Bond, *Catal. Rev. Sci. Eng.*, 39 (1997) 169). However, dopants described so far in the literature usually have negative effects on either the activity or the selectivity of the catalyst.

Very few examples of V/Ti/O catalysts for the oxidation of o-xylene or naphthalene to phthalic anhydride containing tin as dopant are reported. U.S. Pat. No. 4,469,878 mentions the addition of tin as a promoter:

(i) tin is added as the sole promoter to a V/Ti/O catalyst, or alternatively is added together with phosphorus;

(ii) the amount of tin added to the catalyst composition is low: 0.1-1 wt. % of the active components, preferably 0.2-0.6 wt. %.

The performance of the catalyst is not fully satisfactory and in the examples of U.S. Pat. No. 4,469,878 only the oxidation of naphthalene is taken into consideration.

It has been an object of the present invention to provide a catalyst which avoids the disadvantages of the known catalysts for the production of phthalic anhydride and has a very high activity and an excellent selectivity for the formation of phthalic anhydride, especially when o-xylene is used as starting material. It has been another object of the invention to provide a simple and economic process for the preparation of said catalyst starting from easily available inexpensive materials. Still another object of the invention has been to provide a process for the production of phthalic anhydride with high conversion of the starting hydrocarbon(s), high yield and high selectivity.

These objects have been accomplished by the catalyst of the invention, for process of the invention for its preparation and the process of the invention for the production of phthalic anhydride.

Applicants have discovered that the activity of known catalysts can be significantly increased by addition of comparatively large amounts of tin, without any adverse effect on the selectivity to phthalic anhydride. A further finding of the present invention is that the addition of tin is particularly advantageous for the catalyst activity and selectivity if tin is added together with an alkali metal ion, preferably cesium.

The catalysts according to the invention comprise, based on the total weight of the catalytically active oxidic composition (i.e., with disregard of any inert support), from 2 to 15% by weight (calculated as $V_2O_5$) of vanadium and from 1 to 15% by weight (calculated as $SnO_2$) of tin. They further comprise from 70 to 97% by weight (calculated as $TiO_2$) of titanium oxide. This means that unless there are additional components (see below), titanium oxide makes up the balance to 100%.

In a preferred embodiment, the catalyst of the invention contains, based on the catalytically active composition, up to 5% by weight (calculated as $M_2O$) of at least one alkali metal. Preferably, the alkali metal is lithium, potassium or rubidium, and more preferably it is cesium.

In an even more preferred embodiment, cesium is present in an amount of from 0.01 to 2% by weight (calculated as $Cs_2O$), based on the catalytically active composition.

In the finished catalyst, the tin is preferably present in the oxidation state +IV.

Preferably, the titanium oxide which forms the basic ingredient of the catalyst of the invention has the anatase structure and a specific surface area of 10 to 30 $m^2/g$, more preferably 18 to 25 $m^2/g$.

In a particularly preferred embodiment, the catalyst of the invention contains, based on the catalytically active composition, from 4 to 10% by weight (calculated as $V_2O_5$) of vanadium oxide, from 2 to 7% by weight (calculated as $SnO_2$) of tin oxide and from 0.1 to 0.8% by weight (calculated as $Cs_2O$) of cesium oxide.

In another preferred embodiment, the catalyst of the invention contains one or more element(s) selected from the group consisting of lithium, potassium, rubidium, aluminum, zirconium, iron, nickel, cobalt, manganese, silver, copper, chromium, molybdenum, tungsten, iridium, tantalum, niobium, arsenic, antimony, cerium, phosphorus, and mixtures thereof. These elements may be present in a total amount of up to 5% by weight, based on the catalytically active composition.

Advantageously, the catalyst of the invention comprises an inert support whereon the catalytically active composition is deposited in an amount of from 2 to 15%, preferably 3 to 12% by weight, based on the total weight of the catalyst including the support.

Preferably, the inert support consists of pellets or granules consisting of corundum, steatite, alumina, silicon carbide, silica, magnesium oxide, aluminium silicate, and mixtures thereof.

The catalyst of the present invention, which can be used in commercial multitubular reactors, may be prepared according to the following general procedure:

1) A mixture of the ingredients (namely: titanium oxide, vanadium oxide and tin oxide and any additional component such as cesium) of the catalyst's active composition, and/or of precursors which can be converted by thermal treatment into said ingredients is prepared by dissolving, dispersing or suspending said ingredients or precursors in an aqueous or organic solvent, wherein the ingredients and/or precursors are soluble or dispersible.

2) If a supported catalyst shall be prepared, the above solution or suspension (slurry) is coated in the form of a thin layer on an inert support and dried or, if an unsupported catalyst is desired, the solvent contained in the solution or slurry may simply be evaporated and the solid residue dried and/or commninuted, if necessary.

3) The coated support or solid residue obtained in the preceding step is subjected to a final thermal treatment to form the definitive active composition.

Suitable raw materials for the production of the catalyst include:

$TiO_2$ in the form of anatase of suitable surface area, preferably between 10 $m^2/g$ and 30 $m^2/g$, more preferably between 18 $m^2/g$ and 25 $m^2/g$;

vanadium(v) oxide or, as a precursor, any vanadium compound which can be converted by heating into vanadium(v) oxide, such as ammonium metavanadate, vanadium chlorides, vanadium oxychloride, vanadium acetylacetonate and vanadium alkoxides;

tin dioxide or, as a precursor, tin compounds such as metastannic acid, orthostannic acid, tin oxyhydrates, tin chlorides (stannic or stannous) or tin acetate.

Preferred are tin compounds which are easily soluble or couoidally dispersible in the medium employed for catalyst preparation.

Suitable cesium compounds include cesium sulfate, cesium nitrate, cesium chloride and any other commercial cesium salt or compound.

Suitable inert support are materials such as silica, magnesia, silicon carbide, alumnina, aluminium silicate, magnesium silicate (steatite), or other silicates and mixtures thereof. The inert support may be in granular form or in pellet form, usually in the form of spheres, cylinders or rings. The coating of the active compound onto the inert support may be accomplished by spraying the aqueous or organic solution or slurry containing the ingredients and/or precursors on the support. This operation can be carried out in a heated drum, maintained at a temperature which is suitable for the evaporation of the solvent, for example in the range of 50 to 250° C. The ratio between the amount of support and the amount of solution or slurry, and the amount of components dissolved in the solution or suspended in the slurry, are chosen so to reach the amount of active compound which is finally desired.

The final thermal treatment can be carried out in the heated drum mentioned above, or in a separate oven, or directly in the reactor where the selective oxidation of o-xylene, naphthalene or mixtures of the two to phthalic anhydride will take place. The treatment is carried out in air, or other suitable (non-reducing) atmosphere and at a temperature which is typically in the range 250-450° C.

According to the invention, phthalic anhydride is prepared by oxidizing a hydrocarbon selected from the group consisting of o-xylene, naphthalene and mixtures of both in the gas phase at 340 to 400° C. with an oxygen-containing gas, preferably air, in a fixed-bed reactor in the presence of the catalyst of the invention. Advantageously, the oxidation reaction is carried out in a multitubular fixed bed reactor. The catalyst granules are filled into the tubes and the feed prepared by mixing air (or oxygen or any other oxygen-containing gas) with the hydrocarbon (i.e., o-xylene and/or naphthalene) is passed over the catalyst bed.

Preferably, the initial concentration (i.e., the concentration in the reactor feed) of the hydrocarbon is between 0.5 and 2 vol. %.

The (gauge) pressure at the reactor inlet is advantageously slightly higher than atmospheric, preferably between 0.35 and 0.55 bar (absolute pressure: ≈1.35-1.55 bar).

The following non-limiting examples and comparative examples describe preferred embodiments of the invention in relation to catalysts according to prior art:

EXAMPLE 1 (COMPARATIVE EXAMPLE)

$V_2O_5$ (7 wt. %) and $Cs_2O$ (0.5 wt. %) were deposited on titania (anatase) having a surface area of 22.5 $m^2/g$. The catalyst was prepared by dissolution of 9.0 g of $(NH_4)VO_3$ in 2500 ml of hot (60-80° C.) deionized water under stirring. Then $CsNO_3$ (0.069 g) was dissolved in the same, hot solution. The titania (89.5 g) was dropped in the solution and the resulting slurry was loaded in a rotary evaporator to evaporate the solvent. The wet solid was recovered and thermally treated using the following procedure, carried out in static air: Heating from room temperature to 150° C. at a heating rate of 10 K/min; isothermal step at 150° C. for 3 h; then further heating (10 K/min) till a temperature of 450° C. was reached. Final isothermal step at 450° C. for 5 h, and then cooling.

EXAMPLE 2

The same procedure as described in Comparative Example 1 was used, except for the addition of 6.65 g of an aqueous tin oxyhydrate sol (Nyacol Co., grade SN15CG) having a tin content equivalent to 15 wt. % $SnO_2$ and a pH of 10.0. The tin content (as $SnO_2$) in the final catalyst was 1.0 wt.% with respect to the sum of $SnO_2$, $V_2O_5$ and $TiO_2$.

EXAMPLES 3-6

The same procedure as described in Example 2 was used, except for the addition of 20 g, 26.7 g, 33.3 g, and 46.7 g of the $SnO_2$ sol. The tin content (as SnO2) in the final catalysts was 3.0 wt. %, 4.0 wt. %, 5.0 wt. %, and 7.0 wt. %, respectively.

EXAMPLE 7 (COMPARATIVE EXAMPLE)

The same procedure as described in Comparative Example 1 was used, leading to a catalyst with the same composition, except that the surface area of the titania was 18 $m^2/g$.

EXAMPLE 8

The same procedure as described in Example 4, leading to the same final catalyst composition (i.e., 4.0 wt. % $SnO_2$), was used, except that the surface area of the was 18 $m^2/g$ and $SnCl_4$ was used as the Sn compound.

EXAMPLE 9 (COMPARATIVE EXAMPLE)

The same procedure as described in Comparative Example 1, leading to a catalyst with the same composition, was used, except that the surface area of the $TiO_2$ (anatase) was 34 $m^2/g$.

EXAMPLE 10

The same procedure as described in Example 4, leading to the same final catalyst composition, was used, except that the surface area of the $TiO_2$ (anatase) was 34 $m^2/g$ and the Sn compound was $SnCl_4$.

Catalytic Tests

The procedure for catalytic testing was the following: An upright tubular reactor made from stainless steel, with a diameter of 1.25 cm and 25 cm long was first loaded with 11.1 g of inert material (α-alumina, 30-60 mesh particles) and then with 0.23 g of catalyst mixed with 1.0 g of the inert material. The catalyst was shaped in granules having a diameter between 30 and 60 mesh. The feed consisted of o-xylene vapour (1 vol. %) in air, and the flow rate was such to have a residence time, measured at ambient conditions, of 0.3 s. The pressure was atmospheric.

The results obtained are summarized in Table 1. The selectivities to and yields of phthalic anhydride (PA) are given in mole %. It is evident from these results that:

(i) the addition of tin in the range examined (1-7 wt. % $SnO_2$) results in increased activity,
(ii) the highest increase of activity is achieved when the amount of Sn is between about 3 and 5 wt. % $SnO_2$,
(iii) that amount of Sn, and specifically an amount corresponding to 3-4 wt. % of $SnO_2$ also gives a higher maximum yield of PA as compared to a catalyst without tin.

TABLE 1

| Example No. | T [° C.] | Conv. [%] | Sel. PA [%] | Yield PA [%] |
|---|---|---|---|---|
| Comp. 1 | 327 | 26.4 | 61.1 | 16.1 |
|  | 335 | 39.4 | 70.6 | 27.8 |
|  | 347 | 61.5 | 77.0 | 47.4 |
|  | 362 | 78.1 | 82.0 | 64.0 |
|  | 369 | 86.4 | 83.3 | 72.0 |
|  | 375 | 99.1 | 80.6 | 79.9 |
| 2 | 335 | 33.8 | 66.6 | 22.5 |
|  | 347 | 76.1 | 75.7 | 57.6 |
|  | 355 | 93.8 | 75.4 | 70.7 |
|  | 362 | 97.4 | 73.8 | 71.9 |
| 3 | 315 | 20.5 | 54.1 | 11.1 |
|  | 325 | 42.9 | 65.8 | 28.2 |
|  | 335 | 84.9 | 78.1 | 66.3 |
|  | 345 | 100 | 81.3 | 81.3 |
| 4 | 310 | 21.3 | 50.4 | 10.7 |
|  | 320 | 36.2 | 68.6 | 24.8 |
|  | 330 | 84.6 | 85.9 | 72.7 |
|  | 340 | 99.2 | 85.0 | 84.3 |
| 5 | 315 | 23.9 | 54.1 | 12.9 |
|  | 325 | 56.3 | 68.8 | 38.7 |
|  | 335 | 93.1 | 73.2 | 68.1 |
|  | 345 | 99.5 | 71.9 | 71.5 |
| 6 | 337 | 46.0 | 64.9 | 29.8 |
|  | 349 | 75.4 | 77.4 | 58.4 |

TABLE 1-continued

| Example No. | T [° C.] | Conv. [%] | Sel. PA [%] | Yield PA [%] |
|---|---|---|---|---|
| | 360 | 99.5 | 79.8 | 79.4 |
| | 368 | 100 | 77.0 | 77.0 |
| Comp. 7 | 340 | 32.5 | 68.3 | 22.2 |
| | 350 | 63.8 | 78.5 | 50.1 |
| | 360 | 71.9 | 78.3 | 56.3 |
| | 370 | 80.9 | 78.6 | 63.6 |
| 8 | 330 | 18.0 | 48.9 | 8.8 |
| | 339 | 31.8 | 61.0 | 19.4 |
| | 355 | 83.2 | 79.9 | 66.5 |
| | 365 | 96.5 | 81.3 | 78.5 |
| | 371 | 100 | 81.5 | 81.5 |
| Comp. 9 | 322 | 23.9 | 59.8 | 14.3 |
| | 326 | 46.3 | 71.0 | 32.9 |
| | 334 | 76.5 | 78.9 | 60.4 |
| | 342 | 89.3 | 80.7 | 72.1 |
| | 352 | 99.7 | 80.1 | 79.8 |
| 10 | 295 | 4.9 | 32.4 | 1.6 |
| | 310 | 9.6 | 40.7 | 3.9 |
| | 322 | 24.2 | 56.6 | 13.7 |
| | 334 | 95.8 | 79.6 | 76.2 |
| | 340 | 100 | 81.0 | 81.0 |

The invention claimed is:

1. An oxidic catalyst for the production of phthalic anhydride by oxidizing a hydrocarbon selected from the group consisting of o-xylene naphthalene, and mixtures thereof, which catalyst comprises, based on the catalytically active composition, from 2 to 15% by weight (calculated as $V_2O_5$) of vanadium, from 1 to 15% by weight (calculated as $SnO_2$) of tin, from 70 to 97% by weight (calculated as $TiO_2$) of titanium oxide.

2. The catalyst of claim 1 which further contains, based on the catalytically active composition, up to 5% by weight (calculated as $M_2O$) of at least one alkali metal.

3. The catalyst of claim 2 wherein the alkali metal is cesium.

4. The catalyst of claim 3 wherein the cesium is present in an amount of from 0.01 to 2% by weight (calculated as $Cs_2O$), based on the catalytically active composition.

5. The catalyst of claim 1 wherein the tin is present in the oxidation state +IV.

6. The catalyst of claim 1 wherein the titanium oxide has a specific surface area of 10 to 30 $m^2/g$, preferably 18 to 25 $m^2/g$, and the anatase structure.

7. The catalyst of claim 1 wherein the catalytically active composition contains from 4 to 10% by weight (calculated as $V_2O_5$) of vanadium oxide, from 2 to 7% by weight (calculated as $SnO_2$) of tin oxide and from 0.1 to 0.8% by weight (calculated as $Cs_2O$) of cesium oxide.

8. The catalyst of claim 1 which further contains at least one element selected from the group consisting of lithium, potassium, rubidium, aluminium, zirconium, iron, nickel, cobalt, manganese, silver, copper, chromium, molybdenum, tungsten, iridium, tantalum, niobium, arsenic, antimony, cerium, phosphorus and mixtures thereof in an amount of up to 5% by weight, based on the catalytically active composition.

9. The catalyst of claim 1 wherein the catalytically active composition is coated on an inert support in an amount of 2 to 15% by weight, preferably 3 to 12% by weight, based on the total weight of the catalyst.

10. The catalyst of claim 9 wherein the inert support consists of pellets or granules of at least one material selected from the group consisting of corundum, steatite, alumina, silicon carbide, silica, magnesium oxide, aluminium silicate and mixtures thereof.

11. A process for the production of phthalic anhydride comprising the oxidation of a hydrocarbon selected from the group consisting of o-xylene, naphthalene and mixtures of o-xylene and naphthalene in the gas phase at 340 to 400° C. with an oxygen-containing gas in a fixed-bed reactor in the presence of a catalyst according to claim 1.

12. The process of claim 11 wherein the initial concentration of the hydrocarbon in the gas phase is 0.5 to 2.0% by volume.

13. The process of claim 11 wherein the gauge pressure at the entrance of the reactor is 0.35 to 0.55 bar.

14. The catalyst of claim 4 wherein the tin is present in the oxidation state +IV.

15. The catalyst of claim 5 wherein the titanium oxide has a specific surface area of 10 to 30 $m^2/g$, preferably 18 to 25 $m^2/g$, and the anatase structure.

16. The catalyst of claim 6 wherein the catalytically active composition contains from 4 to 10% by weight (calculated as $V_2O_5$) of vanadium oxide, from 2 to 7% by weight (calculated as $SnO_2$) of tin oxide and from 0.1 to 0.8% by weight (calculated as $Cs_2O$) of cesium oxide.

17. The catalyst of claim 7 which further contains at least one element selected from the group consisting of lithium, potassium, rubidium, aluminium, zirconium, iron, nickel, cobalt, manganese, silver, copper, chromium, molybdenum, tungsten, iridium, tantalum, niobium, arsenic, antimony, cerium, phosphorus and mixtures thereof in an amount of up to 5% by weight, based on the catalytically active composition.

18. The catalyst of claim 8 wherein the catalytically active composition is coated on an inert support in an amount of 2 to 15% by weight, preferably 3 to 12% by weight, based on the total weight of the catalyst.

19. A process for the production of phthalic anhydride comprising the oxidation of a hydrocarbon selected from the group consisting of o-xylene, naphthalene and mixtures of o-xylene and naphthalene in the gas phase at 340 to 400° C. with an oxygen-containing gas in a fixed-bed reactor in the presence of a catalyst according to claim 10.

20. The process of claim 12 wherein the gauge pressure at the entrance of the reactor is 0.35 to 0.55 bar.

* * * * *